(12) United States Patent
Jenck

(10) Patent No.: US 9,532,985 B2
(45) Date of Patent: Jan. 3, 2017

(54) TETRAHYDROQUINOLINE DERIVATIVES FOR TREATING POST-TRAUMATIC STRESS DISORDERS

(75) Inventor: Francois Jenck, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 756 days.

(21) Appl. No.: 12/681,802

(22) PCT Filed: Oct. 9, 2008

(86) PCT No.: PCT/IB2008/054138
§ 371 (c)(1),
(2), (4) Date: Apr. 6, 2010

(87) PCT Pub. No.: WO2009/047723
PCT Pub. Date: Apr. 16, 2009

(65) Prior Publication Data
US 2010/0234420 A1 Sep. 16, 2010

(30) Foreign Application Priority Data
Oct. 10, 2007 (WO) .................. PCT/IB2007/054130

(51) Int. Cl.
*A61K 31/472* (2006.01)
*A61K 31/4725* (2006.01)

(52) U.S. Cl.
CPC ......... *A61K 31/4725* (2013.01); *A61K 31/472* (2013.01)

(58) Field of Classification Search
CPC ........................... A61K 31/472; A61K 31/4725
See application file for complete search history.

(56) References Cited

U.S. PATENT DOCUMENTS

| 6,703,392 B2 | 3/2004 | Aissaoui et al. |
| 2003/0176415 A1 | 9/2003 | Aissaoui et al. |
| 2006/0178515 A1 | 8/2006 | Aissaoui et al. |
| 2007/0160538 A1 | 7/2007 | Sawai et al. |
| 2007/0191424 A1 | 8/2007 | Aissaoui et al. |
| 2009/0082394 A1 | 3/2009 | Jenck |

FOREIGN PATENT DOCUMENTS

| EP | 2 402 322 A1 | 1/2012 |
| WO | WO 01/68609 | 9/2001 |
| WO | WO 2004085403 | 10/2004 |
| WO | WO 2007/105177 | 9/2007 |

OTHER PUBLICATIONS

Rose et al. "Psychological debriefing for preventing post-traumatic stress disorder (PTSD)" Cochran Database of Systemic Reviews, 2002, issue 2, pp. 1-47.*

Ipser et al. "Pharmacotherapy for prevention of post-traumatic stress disorder" Cochran Database of Systematic Reviews, 2006, issue 4, pp. 1-11.*
Friedman, M.J., "Drug Treatment for PTSD" Annals New York Academy of Sciences, 1997, vol. 821, pp. 359-371.*
Davidson JR "Treatment of posttraumatic stress disorder: the impact of paroxetine" Psychopharmacology Bulletin, 2003, vol. 37 Suppl 1, pp. 76-88.*
Jones et al. "Effects of centrally administered orexin-B and orexin-A a role for orexin-1 receptors in orexin-B induced hyperactivity" Psychopharmacology 2001, vol. 153, pp. 210-218.*
Hagan et al. "Orexin A activates locus coeruleus cell firing and incrases arousal in the rat" Proc. Natl. Acad. Sci., 1999, vol. 96, pp. 10911-10916.*
Johnson et al. "A key role for orexin in panic anxiety" Nature medicine, 2010, vol. 16, pp. 111-115.*
Brisbare-Roch, et al., "Promotion of Sleep by Targeting the Orexin System in Rats, Dogs, and Humans", Nature Medicine, vol. 13, pp. 150-155, (2007).
Brisbare-Roch, et al., "Transient Orexin Receptor Blockade Induces Sleep Without Cataplexy in Rats", Sleep and Biological Rhythms, vol. 5, (S1), A78 Poster 270 at the World Sleep Congress, Cairns, Sep. 2007.
Jenck F., et al., "Somnolence Induced by Pharmalogical Blockade of Both Orexin OX1 and OX2 Receptors in Dogs Sleep and Biological Rhythms" (Poster) (S1), A79 Poster 271 at the World Sleep Congress, Cairns, Sep. 2007.
Hoever, P., et al., "Entry-into-Humans Study with Almorexant (ACT-078573), a Dual Orexin Receptor Antagonist: Tolerability, Safety, and Pharmacokinetics Sleep and Biological Rhythms" 2007, 5(S1): A131 Poster 444 at the World Sleep Congress, Cairns, Sep. 2007.

(Continued)

*Primary Examiner* — Kendra D Carter
(74) *Attorney, Agent, or Firm* — Hoxie & Associates LLC

(57) ABSTRACT

The invention relates to methods of treating, reducing the symptoms of, or preventing a post-traumatic stress syndrome by administration of tetrahydroquinoline derivatives of formula I

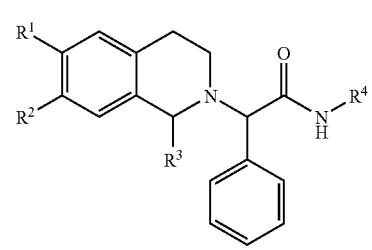

wherein
$R^1$ and $R^2$ each independently represent $(C_1-C_4)$alkoxy,
$R^3$ represents aryl-$(C_1-C_4)$alkyl or heteroaryl-$(C_1-C_4)$alkyl, and
$R^4$ represents hydrogen or $(C_1-C_4)$alkyl,
or pharmaceutically acceptable salts thereof.

2 Claims, 1 Drawing Sheet

(56) References Cited

OTHER PUBLICATIONS

Hoever, P., et al., Entry-into-Humans Study with Almorexant (ACT-078573), A Dual Orexin Receptor Antagonist: Pharmacodynamics Sleep and Biological Rhythms 2007, 5 (S1): A131 Poster 443 at the World Sleep Congress, Cairns, Sep. 2007.

Dingemanse, J., et al., Proof-of-Concept Study in Primary Insomnia Patients with Almorexant (ACT-078573), a Dual Orexin Receptor Antagonist Sleep and Biological Rhythms, 2007, 5: A194 Poster 653 at the World Sleep Congress, Cairns, Sep. 2007.

Jenck, F., et al., Correspondence of "Promotion of Sleep by Targeting the Orexin System in Rats, Dogs and Humans", Nature Medicine, vol. 13, pp. 525-526, 2007.

Brisbare-Roch, C., et al., Effects of Repeated Oral Administration of the Orexin Receptor Antagonist Almorexant in Male Rats and Dogs, Sleep 2008, 31: A38 Poster 0118 at the US Associated Professional Sleep Societies Meeting, Baltimore, Jun. 2008.

Hoever, P., et al., Multiple-Dose Pharmacokinetics, Pharmacodynamics, Safety, and Tolerability of the Orexin Receptor Antagonist Almorexant in Healthy Subjects, Sleep 2008, 31: A38 Poster 0116 at the US Associated Professional Sleep Societies Meeting, Baltimore, Jun. 2008.

Jenck, F., et al., "Promotion of Sleep Though an Orally Available Hypocretin/Orexin Antagonist in Rats, Dogs and Humans", Eur. Neuropsychopharm2008, 18 (Suppl 4): S158 Abstract: Lecture at the European College of Neuropsychopharmacology (ECNP) meeting, Barcelona, Sep. 2008.

Furlong, T.M., et al., "Hypocretin/Orexin Contributes to the Expression of Some but not All Forms of Stress and Arousal", European Joural of Neuroscience, 2009, AOP: Oct. 7, 2009.

Sakurai, T., "The Nerual Circuit of Orexin (Hypocretin): Maintaining Sleep and Wakefulness", Nature Reviews, Neuroscience, vol. 8, pp. 171-178, 2007.

Kozaric-Kovacic; "Psychopharmacotherapy of Posttraumatic Stress Disorder", Croatian Medical Journal, vol. 49; No. 4; 2008; 459-475.

Jeffreys, M., "Clinician's Guide to Medications for PTSD," U.S. Department of Veterans Affairs, Date Created: Jan. 7, 2009, Reviewed/Updated Date: Jul. 23, 2012, http://www.ptsd.va.gov/professional/pages/clinicians-guide-to-medications-for-ptsd.asp, 8 pages.

Schnurr, P. et al., "Treatments for PTSD: Understanding the Evidence," PTSD Research Quarterly, 2008, vol. 19, No. 3, ISSN: 1050-1835, 12 pages.

Stein, D. et al., "Pharmacotherapy for Post Traumatic Stress Disorder (PTSD) (Review)," Cochrane Database of Systematic Reviews, 2006, Issue 1, 112 pages.

Foa, E. et al., Eds., "Treatment of Posttraumatic Stress Disorder," The Journal of Clinical Psychiatry, 1999, 60 (Supplement 16), 4-76.

Notification of Reasons for Refusal for Japanese Patent Application No. 2010-528515 mailed Jun. 12, 2013, 6 pages (3 pages of Notification of Reasons for Refusal, 3 pages of translation).

Bunshi-Seishin-Igaku, Japanese Journal of Molecular Psychiatry, 2002, 2 (3), 243-249.

Rinsyo-Seishin-Igaku, Japanese Journal of Clinical Psychiatry, 2000, 29 (1), 35-40.

\* cited by examiner

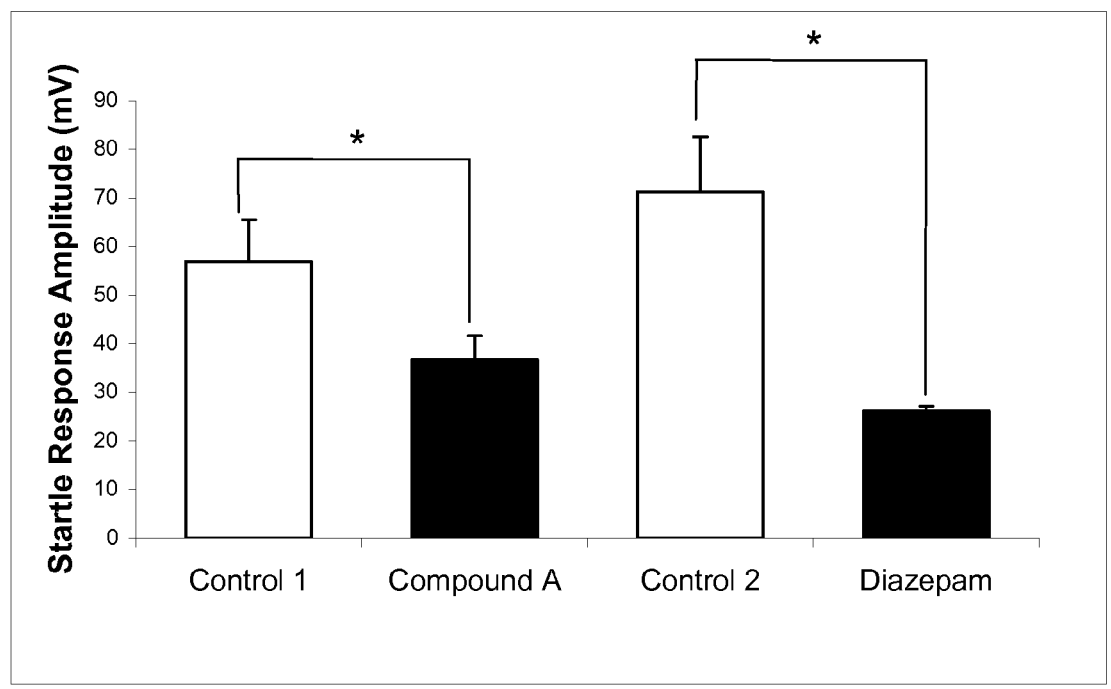

TETRAHYDROQUINOLINE DERIVATIVES FOR TREATING POST-TRAUMATIC STRESS DISORDERS

CROSS REFERENCE TO RELATED APPLICATIONS

This application is a United States Application under 35 U.S.C. 371 claiming benefit of PCT Application No. PCT/IB2008/054138, filed on Oct. 9, 2008, which claims the benefit of PCT Application No. PCT/IB2007/054130, filed on Oct. 10, 2007 the contents of each of which are incorporated herein by reference.

The present invention concerns the use of tetrahydroquinoline derivatives for the preparation of a medicament for preventing or treating post-traumatic stress disorders, as well as said tetrahydroquinoline derivatives for the prevention or the treatment of a post-traumatic stress disorder.

Human anxiety is a set of complex and interrelated forms of abnormal emotional reactions to particular environmental conditions. Human anxiety has been subdivided into five subtypes of anxiety disorders on the basis of differences in clinical expression and neurobiological substrate; these subtypes include: generalized anxiety disorders (GAD), panic anxiety disorders (PADs), phobic anxieties (PHOBs), obsessive-compulsive disorders (OCDs) and post-traumatic stress disorders (hereafter abbreviated PTSDs).

Orexin receptor antagonists are a novel type of nervous system or psychotropic drugs that decrease alertness and promote sleep. Their mode of action in animals and humans involves blockade of orexin receptors in the brain and modulation of sleep and arousal systems. Orexin receptor antagonists are currently developed for use in the treatment of sleep disorders and insomnias.

WO 01/68609 and WO 2005/118548 disclose that certain tetrahydroquinoline derivatives, including the compounds of formula I described below, are orexin receptor antagonists and can be used for the treatment of anxiety in general. However, US 2007/0160538 A1 discloses the use of orexin receptor antagonists (including the compounds of formula I mentioned below) for the treatment of several types of anxiety, but specifically excluding stress-related anxieties (and notably PTSDs).

It was now surprisingly discovered that, despite the teaching of US 2007/0160538 A1, the orexin receptor antagonists of formula I hereafter can be used for the preparation of a medicament, and are suitable, for the prevention or treatment of PTSDs.

Various embodiments of the invention are presented hereafter:

i) According to this invention, the compounds of formula I

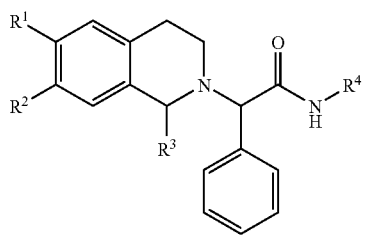

I wherein
R¹ and R² each independently represent $(C_1\text{-}C_4)$alkoxy,
R³ represents aryl-$(C_1\text{-}C_4)$alkyl or heteroaryl-$(C_1\text{-}C_4)$alkyl, and
R⁴ represents hydrogen or $(C_1\text{-}C_4)$alkyl,
or the pharmaceutically acceptable salts of said compounds of formula I, can be used for the preparation of a medicament, and are suitable, for the prevention or treatment of a PTSD.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a saturated straight or branched chain alkyl group, containing from one to four carbon atoms. Representative examples of alkyl groups include methyl, ethyl, propyl, iso-propyl, n-butyl, iso-butyl, sec-butyl and tert-butyl. The term "$(C_x\text{-}C_y)$alkyl" (x and y being two different integers) refers to a straight or branched chain alkyl group containing x to y carbon atoms.

The term "alkoxy", used alone or in combination, refers to a saturated straight or branched chain alkoxy group, containing from one to four carbon atoms. Representative examples of alkoxy groups include methoxy, ethoxy, propoxy, iso-propoxy, n-butoxy, iso-butoxy, sec-butoxy and tert-butoxy. The term "$(C_x\text{-}C_y)$alkoxy" (x and y being two different integers) refers to a straight or branched chain alkoxy group containing x to y carbon atoms.

The term "halogen" refers to fluorine, chlorine, bromine or iodine, preferably to fluorine or chlorine.

The term "aryl" refers to a phenyl group, which may be substituted one to three times by substituents each independently selected from the group consisting of halogen, alkyl, alkoxy, trifluoromethyl and trifluoromethoxy. Representative examples of aryl include, but are not limited to, phenyl, 4-trifluoromethyl-phenyl, 2-fluoro-phenyl, 3-fluoro-phenyl, 4-fluoro-phenyl, 2-chloro-phenyl, 3-chloro-phenyl, 4-chloro-phenyl, 2-methyl-phenyl, 3-methyl-phenyl, 4-methyl-phenyl, 2-methoxy-phenyl, 3-methoxy-phenyl and 4-methoxy-phenyl.

The term aryl-$(C_x\text{-}C_y)$alkyl (x and y being two different integers) refers to a $(C_x\text{-}C_y)$alkyl group as previously defined in which one hydrogen atom has been replaced by an aryl group as previously defined. Representative examples of aryl-$(C_1\text{-}C_4)$alkyl groups include, but are not limited to, benzyl, 2-phenyl-ethyl and 2-(4-trifluoromethyl-phenyl)-ethyl.

The term heteroaryl, alone or in combination, means a 5- to 10-membered monocyclic or bicyclic aromatic ring containing 1, 2 or 3 heteroatoms selected from oxygen, nitrogen and sulphur which may be the same or different. A heteroaryl group can be unsubstituted or substituted with up to three substituents independently selected from halogen, $(C_1\text{-}C_4)$alkyl, $(C_1\text{-}C_4)$alkoxy, trifluoromethyl or trifluoromethoxy. Examples of such heteroaryl groups are pyridyl, pyrimidinyl, pyrazinyl, pyridazinyl, quinolinyl, isoquinolinyl, thienyl, thiazolyl, isothiazolyl, furyl, imidazolyl, pyrazolyl, pyrrolyl, indazolyl, indolyl, isoindolyl, benzimidazolyl, isoxazolyl, oxazolyl, oxadiazolyl, thiadiazolyl, quinoxalinyl, phthalazinyl, cinnolinyl, isobenzofuranyl. A preferred heteroaryl group is pyridyl, which might be unsubstituted or substituted once with methyl, ethyl or methoxy.

The term heteroaryl-($C_x$-$C_y$)alkyl (x and y being two different integers) refers to a ($C_x$-$C_y$)alkyl group as previously defined in which one hydrogen atom has been replaced by a heteroaryl group as previously defined. Representative examples of heteroaryl-($C_1$-$C_4$)alkyl groups include, but are not limited to, 2-(pyridin-3-yl)-ethyl optionally substituted once on the pyridine ring with methyl, methoxy, chlorine or trifluoromethyl.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

ii) According to a preferred embodiment of this invention, the compounds of formula I as defined in embodiment i) above, or their pharmaceutically acceptable salts, will be such that $R^1$ represents methoxy or ethoxy (and preferably methoxy).

iii) According to another preferred embodiment of this invention, the compounds of formula I as defined in embodiment i) or ii) above, or their pharmaceutically acceptable salts, will be such that $R^2$ represents methoxy or ethoxy (and preferably methoxy).

iv) According to one variant of the invention, the compounds of formula I as defined in embodiment i), ii) or iii) above, or their pharmaceutically acceptable salts, will be such that $R^3$ represents aryl-($C_1$-$C_4$)alkyl.

v) According to one subvariant of embodiment variant iv) above, the compounds of formula I as defined in embodiment iv) above, or their pharmaceutically acceptable salts, will be such that $R^3$ represents 4-trifluoromethyl-phenyl-methyl, 2-(4-trifluoromethyl-phenyl)-ethyl or 3-(4-trifluoromethyl-phenyl)-propyl (and especially 2-(4-trifluoromethyl-phenyl)-ethyl).

vi) According to another variant of the invention, the compounds of formula I as defined in embodiment i), ii) or iii) above, or their pharmaceutically acceptable salts, will be such that $R^3$ represents heteroaryl-($C_1$-$C_4$)alkyl.

vii) According to one subvariant of embodiment variant vi) above, the compounds of formula I as defined in embodiment vi) above, or their pharmaceutically acceptable salts, will be such that $R^3$ represents (4-trifluoromethyl-3-pyridyl)-methyl, 2-(4-trifluoromethyl-3-pyridyl)-ethyl or 3-(4-trifluoromethyl-3-pyridyl)-propyl (and especially 2-(4-trifluoromethyl-3-pyridyl)-ethyl).

viii) According a further preferred embodiment of this invention, the compounds of formula I as defined in one of embodiments i) to vii) above, or their pharmaceutically acceptable salts, will preferably be such that $R^4$ represents ($C_1$-$C_4$)alkyl (more preferably ($C_1$-$C_3$)alkyl, notably methyl or ethyl and in particular methyl).

ix) In a general manner, the compounds of formula I according to any one of embodiments i) to viii) used or suitable for the prevention or treatment of PTSDs, or their pharmaceutically acceptable salts, will be such that the configuration of the carbon atom bearing the phenyl group is (R) and that the configuration of the carbon atom bearing the radical $R^3$ is (S), that is, the compounds of formula I will have the configuration Ia depicted below

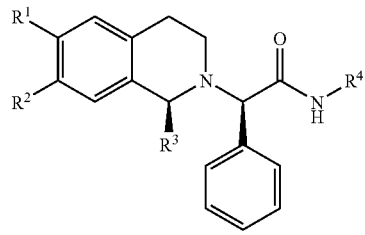

x) According to a particularly preferred variant of embodiments i) to v) and viii) or ix), the compound of formula I used or suitable for the prevention or treatment of PTSDs, or its pharmaceutically acceptable salt, will be 2-{6,7-dimethoxy-1-[2-(4-trifluoromethyl-phenyl)-ethyl]-3,4-dihydro-1H-isoquinolin-2-yl}-N-methyl-2-phenyl-acetamide or one of its pharmaceutically acceptable salts.

xi) According to a preferred subembodiment of embodiment x), the compound of formula I used or suitable for the prevention or treatment of PTSDs, or its pharmaceutically acceptable salt, will be (R)-2-{(S)-6,7-dimethoxy-1-[2-(4-trifluoromethyl-phenyl)-ethyl]-3,4-dihydro-1H-isoquinolin-2-yl}-N-methyl-2-phenyl-acetamide or one of its pharmaceutically acceptable salts (and especially (R)-2-{(S)-6,7-dimethoxy-1-[2-(4-trifluoromethyl-phenyl)-ethyl]-3,4-dihydro-1H-isoquinolin-2-yl}-N-methyl-2-phenyl-acetamide hydrochloride).

xii) Another embodiment of this invention relates to a method of treating a patient affected by a PTSD, said method comprising the administration of a compound of formula I as defined in embodiment i) above, or a pharmaceutically acceptable salt thereof, in an amount sufficient to treat said PTSD.

xiii) Yet another embodiment of this invention relates to a method of reducing the symptoms of a patient affected by a PTSD, said method comprising the administration of a compound of formula I as defined in embodiment i) above, or a pharmaceutically acceptable salt thereof, in an amount sufficient to reduce the symptoms of the PTSD in said patient.

xiv) A further embodiment of this invention relates to a method of preventing, in a patient susceptible to be affected by a PTSD, the occurrence of the PTSD said method comprising the administration of a compound of formula I as defined in embodiment i) above, or a pharmaceutically acceptable salt thereof, in an amount sufficient to prevent the occurrence of the PTSD in said patient.

xv) Yet a further embodiment of this invention relates to a method of reducing, in a patient susceptible to be affected by a PTSD (that is, a person having been subject to traumatic stress), the symptoms of the PTSD, said method comprising the administration of a compound of formula I as defined in embodiment i) above, or a pharmaceutically acceptable salt thereof, in an amount sufficient to reduce the symptoms of the PTSD in said patient.

Concerning the methods corresponding to embodiments xii) to xv) above, the preferences mentioned regarding the compounds of formula I and their pharmaceutically acceptable salts in embodiments i) to xi) above are applicable mutatis mutandis to said methods.

The compounds of formula I and their pharmaceutically acceptable salts can be prepared by methods known to one skilled in the art (see e.g. WO 01/68609 and WO 2005/118548).

The compounds of formula I and their pharmaceutically acceptable salts can be used as medicaments for the prevention or treatment of PTSDs, e.g. in the form of pharmaceutical compositions for enteral or parenteral administration.

The production of the pharmaceutical compositions can be effected in a manner which will be familiar to any person skilled in the art (see for example Remington, The Science and Practice of Pharmacy, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The dose of a compound or pharmaceutically acceptable salt according to the present invention, to be provided for the treatment of PTSDs, varies according to the administration method, the age and body weight of the subject to be treated as well as the state of the latter, and will be finally decided by the attending doctor. As an indication, the amount of a compound of formula I contemplated to be given to the patient to reduce or eliminate the symptoms of PTSDs, either preventively or curatively, is from 1 mg to 1000 mg per day (i.e. from 0.015 to 15 mg/kg body weight per day), particularly from 5 mg to 500 mg per day (i.e. 0.075 to 7.5 mg/kg per day) and more particularly from 10 mg to 200 mg per day (i.e. 0.15 to 3 mg/kg per day).

Particular embodiments of the invention are described in the following Example, which serves to illustrate the invention in more detail without limiting its scope in any way.

Pharmacological Properties of the Invention Compounds

Effect of a Compound of Formula I on Fear-Potentiated Startle Response in Rats

Experimental Methods:

The compounds of formula I can be administered to the animal in order to assess their effects on emotional reactivity. A decrease in reactivity, relative to the absence of the test agents, indicates that the administered compound reduces fear and anxiety. As used herein, a "control mammal" can be an untreated mammal (i.e. an animal receiving no agents or not the same combinations to be assessed), and/or a trained control mammal (i.e. a mammal that undergoes training to demonstrate a learned behaviour).

Signs of decreased emotional reactivity to acoustic stimuli have been discovered in an animal model of fear potentiated acoustic startle. Anxiolytic-like activity—as assessed by decreased acoustic startle reactivity—was observed one hour after treatment with a compound of the formula I compared to vehicle (PEG400) control treatment and to active treatment with diazepam given orally. This was observed in the Fischer F344 strain of laboratory rats characterized by a particular degree of emotional reactivity.

In human medicine, increased acoustic startle reactivity has been observed in patients suffering from PTSD anxiety compared to healthy subjects (Exaggerated acoustic startle reflex in Gulf War veterans with posttraumatic stress disorder, *Am. J. Psychiatry* (1996), 153(1), 64-68).

In the fear-potentiated startle procedure in rats, a neutral stimulus such as light is repetitively paired with an aversive stimulus such as mild foot shock. When an animal is presented with loud acoustic stimuli, enhanced startle responses are elicited when the startle stimulus is preceded by the light (a classically conditioned increase in fear). Benzodiazepine anxiolytics attenuate the response enhancement. Startle response was recorded by using auditory startle chambers. After a 95-dB habituation session in the dark, 10 randomly alternating acoustic stimuli of 90, 95, or 105 dB (50-ms duration) were given in the presence or absence of light. Startle response amplitudes for each trial type were averaged for each rat across the entire test session.

Results:

The results obtained after performing the test described above on four groups of rats:

a first group of 12 rats (called "control 1" in FIG. 1) that have been treated with the vehicle only, a second group of 12 rats (called "Compound A" in FIG. 1) that have received oral treatment by 107 mg/kg of (R)-2-{(S)-6,7-dimethoxy-1-[2-(4-trifluoromethyl-phenyl)-ethyl]-3,4-dihydro-1H-isoquinolin-2-yl}-N-methyl-2-phenyl-acetamide hydrochloride, a third group of 16 rats (called "control 2" in FIG. 1) that have been treated with the vehicle only, and a fourth group of 12 rats (called "Diazepam" in FIG. 1), that have received oral treatment by 3 mg/kg diazepam, have been summarised in FIG. 1.

As one can see, oral treatment by (R)-2-{(S)-6,7-dimethoxy-1-[2-(4-trifluoromethyl-phenyl)-ethyl]-3,4-dihydro-1H-isoquinolin-2-yl}-N-methyl-2-phenyl-acetamide hydrochloride (compound A, to be compared with rats of the group "control 1"), like oral treatment by diazepam (to be compared with rats of the group "control 2"), reduces in a significant manner the startle response amplitude in Fischer F344 rats.

The invention claimed is:

1. A method of treating an increased startle response in a patient having a post-traumatic stress disorder, said method comprising the administration of (R)-2-{(S)-6,7-dimethoxy-1-[2-(4-trifluoromethyl-phenyl)-ethyl]-3,4-dihydro-1H-isoquinolin-2-yl}-N-methyl-2-phenyl-acetamide or one of its pharmaceutically acceptable salts to the patient.

2. A method according to claim 1, wherein the compound is (R)-2-{(S)-6,7-dimethoxy-1-[2-(4-trifluoromethyl-phenyl)-ethyl]-3,4-dihydro-1H-isoquinolin-2-yl}-N-methyl-2-phenyl-acetamide hydrochloride.

* * * * *